United States Patent [19]

Farooq

[11] 4,287,204
[45] Sep. 1, 1981

[54] 1,3-BENZODITHIOL-2-ONES
[75] Inventor: Saleem Farooq, Ettingen, Switzerland
[73] Assignee: Ciba-Geigy Corporation, Ardsley, N.Y.
[21] Appl. No.: 140,537
[22] Filed: Apr. 15, 1980
[30] Foreign Application Priority Data
  Apr. 25, 1979 [CH] Switzerland .......................... 3888/79
  Nov. 21, 1979 [CH] Switzerland ....................... 10388/79
[51] Int. Cl.³ .................... A01N 43/28; C07D 339/06
[52] U.S. Cl. ..................................... 424/277; 549/33; 564/440; 564/441
[58] Field of Search .......................... 549/33; 424/277
[56]  References Cited
  U.S. PATENT DOCUMENTS
  4,084,954  4/1978  Rasheed et al. ................. 260/326.62
  4,187,096  2/1980  Rasheed et al. ....................... 549/33

Primary Examiner—Henry R. Jiles
Assistant Examiner—Natalia Harkaway
Attorney, Agent, or Firm—Frederick H. Rabin; John J. Maitner

[57]  ABSTRACT

Novel N-substituted 7-amino-6-nitro-4-trifluoromethyl-1,3-benzodithiol-2-ones of the formula

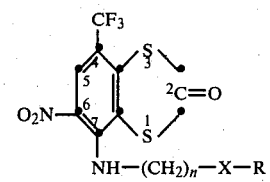

wherein X is —O— or —S—, R is $C_1$-$C_4$alkyl, $R_1$ is hydrogen or $C_1$-$C_4$alkyl, and n is 2 or 3, processes for the production of these compounds, and compositions containing them for use in pest control, especially for controlling representatives of the order Acarina and insects that are parasites of plants and animals. The novel compounds are especially effective against phytophagous mites.

8 Claims, No Drawings

1,3-BENZODITHIOL-2-ONES

The present invention relates to novel N-substituted 7-amino-6-nitro-4-trifluoromethyl-1,3-benzodithiol-2-ones, processes for their production, and their use in pest control.

The novel N-substituted 7-amino-6-nitro-4-trifluoromethyl-1,3-benzodithiol-2-ones have the formula I

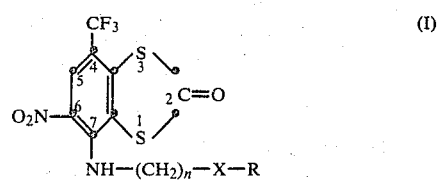

wherein X is —O— or —S—, R is $C_1$–$C_4$alkyl, and n is 2 or 3.

On account of their action, preferred compounds are those of the formula I wherein X is —O—, R is methyl or ethyl, and n is 2 or 3.

1,3-Benzodithiol-2-ones described as having herbicidal, fungicidal, acaricidal, nematocidal and insecticidal properties, are known from German Offenlegungsschrift No. 2 644 036.

Surprisingly, it has now been found that the compounds of the formula I are most effective as agents for controlling representatives of the order Acarina and insects that are parasites of plants and animals, while being well tolerated by plants and having low mammalian toxicity. The compounds of the formula I are suitable in particular for controlling representatives of the order Acarina of the families: Acrididae, Blattidae, Gryllidae, Gryllotalpidae, Tettigoniidae, Cimicidae, Pyrrhocoridae, Reduviidae, Aphididae, Delphacidae, Diaphididae, Pseudococcidae, Chrysomilidae, Coccinellidae, Bruchidae, Scarabaeidae, Dermestidae, Tenebrionidae, Curculionidae, Tincidae, Noctuidae, Lymantriidae, Pyralidae, Galleridae, Culicidae, Tipulidae, Stomoxydae, Muscidae, Calliphoridae, Trypetidae, Pulicidae.

Owing to their good acaricidal properties, the compounds of the formula I are also suitable for controlling ectoparasites in domestic animals and productive livestock, e.g. by treating animals, cowsheds, barns, stables etc., and pastures.

Of especial importance is the fact that the compounds of the formula I have a surprisingly potent and specific action against plant-parasitic mites and mites which are parasites of animals. Thus the compounds of the formula I can be employed for controlling Phytophagous mites e.g. of the families Tetranychidae and Phytoptipalpidae (spider mites), Tarsonemidae (soft-bodied mites) and Eriophydiae (gall mites). The compounds of formula I are suitable in particular for controlling the following species of mites which infest crops of fruit and vegetables: *Tetranychus urticae, Tetranychus cinnabarinus, Panonychus ulmi, Bryobia rubrioculus, Panonychus citri, Eriophyes pyri, Eriophyes ribis, Eriophyes vitis, Tarsomemus pallidus, Phyllocoptes vitis* and *Phyllocoptura oleivora*. With the aid of compounds of formula I it is also possible to control parasitic mites e.g. of the families Sarcoptidae, Psoroptidae, Dermanyssidae and Demodicidae, in particular scab mites of the species *Sarcoptes scabiei* and *Notoedres cati*, which penetrate deep into the epidermis as far as the nerve ends of domestic animals and productive livestock infested by them and cause severe irritation and damage, and also mites of the species *Dermanyssus gallinae* and *Psoroptes ovis*.

The compounds of the formula I can be obtained by methods which are known per se (cf. German Offenlegungsschrift No. 2 644 036; J. Org. Chem. 42, 1265 and 44, 267), wherein the benzodithiol-2-one ring system is formed in only one process step. To this end, a suitably substituted benzotrifluoride of the formula II

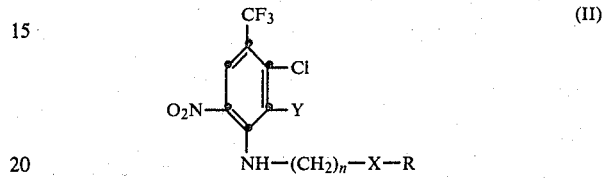

is reacted with a N,N-dialkyldithiocarbamic acid of the formula III or a salt thereof, or with the corresponding dihydrate

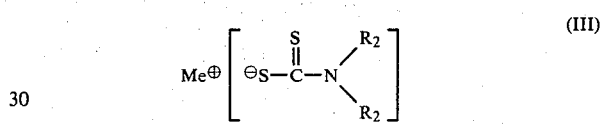

In formulae II and III above, X, R and n are as defined for formula I, $R_2$ is a $C_1$–$C_4$alkyl radical, Y is nitro or halogen, and $Me^\oplus$ is a hydrogen ion or a monovalent cation, preferably an ion of an alkali metal, e.g. $Na^\oplus$.

The above reaction is preferably carried out under normal pressure and ordinarily within the temperature range from 10° to 150° C., with the preferred range being from 50° to 100° C. The reaction often goes even at room temperature; but a higher temperature is also often desirable in order to speed up the reaction. It is preferred to carry out the reaction in a solvent, although the solvent can also be omitted if the starting materials are able to go into solution on their own. It is possible to employ any solvent which is inert to the reactants and in which these are soluble to a certain degree. Examples of suitable solvents are dimethyl formamide, dimethyl sulfoxide, and ketones such as acetone and methyl isobutyl ketone. The molar ratio of the reactants is usually 1:1. It is generally preferred, however, to use a slight excess of N,N-dialkyldithiocarbamic acid in order to ensure as complete a reaction as possible.

The N,N-dialkyldithiocarbamic acids of the formula III and their salts are known (cf. J. Org. Chem. 41, 3564). The substituted benzotrifluorides of the formula II which are suitable starting materials for the above process have not yet been described, however, and can be obtained by reaction of the corresponding 4-halobenzotrifluoride of the formula IV with a suitably substituted amine of the formula V, in the presence of a base:

$$\underset{(IV)}{\underset{O_2N}{\overset{CF_3}{\diagdown}}\underset{Y_1}{\diagup}\overset{Cl}{Y}} + H_2N-(CH_2)_n-X-R \longrightarrow$$

$$\underset{(II)}{\underset{O_2N}{\overset{CF_3}{\diagdown}}\underset{NH-(CH_2)_n-X-R}{\diagup}\overset{Cl}{Y}}$$

In the above formulae, X, R and n are as defined for formula I, Y is $NO_2$ or halogen, and $Y_1$ is halogen, preferably chlorine. The manufacture of the compounds of the formula IV is known e.g. from U.S. Pat. No. 3,586,725. The reaction to produce the compounds of the formula II is carried out at a temperature in the range from 0° to 150° C., with the preferred range being from 20° to 80° C., and as a rule using solvents which are inert to the reactants, e.g. aromatic and aliphatic hydrocarbons, halogenated hydrocarbons, alcohols, ketones. A suitable base (acid acceptor) can be an organic base, e.g. a tertiary amine, or an inorganic base, e.g. an alkali metal carbonate. It is also possible to use a further mole of an amine of the formula V as acid acceptor.

The term "halogen" is to be understood as meaning herein chlorine, bromine and iodine, with chlorine being preferred. Possible $C_1$-$C_4$alkyl groups are methyl, ethyl, n-propyl, isopropyl, n-butyl, isobutyl, sec-butyl and tert-butyl.

The action of the compounds of the formula I and the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates and chlorinated hydrocarbons.

Compounds of formula I can also be combined with particular advantage with substances which exert a pesticidally potentiating effect. Examples of such compounds include: piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioate.

The compounds of formula I may be used as pure active ingredient or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions or suspensions, in the conventional formulation which is commonly employed in application technology. Mention may also be made of cattle dips and spray races, in which aqueous preparations are used. These formulations are particularly suitable for controlling pests which are parasites of animals.

The compositions of the present invention are prepared in known manner by homogeneously mixing and/or grinding compounds of formula I with the suitable carriers, with or without the addition of dispersants or solvents which are inert to the active ingredients.

The compounds of formula I may be processed to the following formulations:

Solid formulations dusts, tracking powders and granules (coated granules, impregnated granules and homogeneous granules).

Liquid formulations (a) water-dispersible active ingredient concentrates: wettable powders, pastes and emulsions;
(b) solutions.

The content of active ingredient in the above described compositions is between 0.1% and 95%.

The compounds (active ingredients) of formula I can be formulated e.g. as follows (throughout the present specification all parts and percentages are by weight):

Dust

The following substances are used to formulate (a) a 5% and (b) 2% dust (a)

5 parts of active ingredient,
95 parts of talc;

(b)

2 parts of active ingredient,
1 part of highly disperse silicic acid,
97 parts of talc.

The active ingredients are mixed and ground with the carriers.

Granules

The following substances are used to formulate 5% granules:

5.00 parts of active ingredient,
0.25 part of epoxidised vegetable oil,
0.25 part of cetyl polyglycol ether,
3.50 parts of polyethylene glycol,
91.00 parts of kaolin (particle size 0.3–0.8 mm).

The active ingredient is mixed with the epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable powders

The following constituents are used to formulate (a) a 40%, (b) and (c) a 25%, (d) a 10% wettable powder:

(a)

40 parts of active ingredient,
5 parts of sodium dibutylnaphthalenesulfonate,
54 parts of silicic acid;

(b)

25.0 parts of active ingredient,
4.5 parts of calcium ligninsulfonate, 1.9 parts of Champagne chalk/hydroxyethyl cellulose mixture (1:1),
1.5 parts of sodium dibutylnaphthalenesulfonate,
19.5 parts of silicic acid,
19.5 parts of Champagne chalk,
28.1 parts of kaolin;

(c)

25.0 parts of active ingredient,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur,
46.0 parts of kaolin;

(d)

10 parts of active ingredient,
3 parts of a mixture of the sodium salts of saturated fatty alcohol sulfates,
5 parts of naphthalenesulfonic acid/formaldehyde condensate,
82 parts of kaolin.

The active ingredients are homogeneously mixed with the additives in suitable mixers and the mixture is then ground in appropriate mills and rollers. Wettable powders are obtained which can be diluted with water to give suspensions of the desired concentration.

Emulsifiable concentrates

The following substances are used to formulate (a) a 10%, (b) a 25% and (c) a 50% emulsifiable concentrate:

(a)

10.0 parts of active ingredient,
3.4 parts of epoxidised vegetable oil,
3.4 parts of a combination emulsifier consisting of fatty alcohol polyglycol ether and alkylarylsulfonate/calcium salt,
40.0 parts of dimethyl formamide,
43.2 parts of xylene;

(b)

25.0 parts of active ingredient,
2.5 parts of epoxidised vegetable oil,
10.0 parts of alkylarylsulfonate/fatty alcohol polyglycol ether mixture,
5.0 parts of dimethyl formamide,
57.5 parts of xylene;

(c)

50.0 parts of active ingredient,
4.2 parts of tributylphenol polyglycol ether,
5.8 parts of calcium dodecylbenzenesulfonate,
20.0 parts of cyclohexanone,
20.0 parts of xylene.

By diluting these concentrates with water it is possible to obtain emulsions of the required concentration.

Sprays

The following ingredients are used to formulate (a) a 5% spray, and (b) a 95% spray:

(a)

5 parts of active ingredient,
1 part of epoxidised vegetable oil,
94 parts of ligroin (boiling range 160°-#° C.);

(b)

95 parts of active ingredient,
5 parts of epoxidised vegetable oil.

The invention is further illustrated by the following Examples.

EXAMPLE 1

A solution of 9.5 g (0.053 mole) of N,N-dimethyldithiocarbamic acid (sodium salt dihydrate) in 25 ml of dimethyl sulfoxide is added dropwise at 20° C. in the course of 1 hour to a solution of 18 g (0.052 mole) of 3,5-dinitro-4-[2-methoxyethylamino]-2-chlorobenzotrifluoride in 160 ml of dimethyl sulfoxide, and the batch is stirred for 1½ hours at room temperature. Stirring is then continued for 3 hours at 80° C. (internal temperature). For working up, the reaction mixture is poured on ice-water and extracted three times with ether. The combined ethereal phases are washed four times with water and three times with sodium chloride solution, died over sodium sulfate, filtered, and concentrated. The residue is recrystallised from ether, affording 7-[2-methoxyethylamino]-6-nitro-4-trifluoromethyl-1,3-benzodithiol-2-one with a melting point of 96°-98° C.

Production of starting compounds of the formula II

A solution of 9.8 g (0.131 mole) of 2-methoxyethylamine in 20 ml of chloroform is added dropwise at 0°-5° C. to a solution of 20 g (0.065 mole) of 2,4-dichloro-3,5-dinitro-benzotrifluoride in 40 ml of chloroform. The reaction mixture is stirred for 2 hours at 0°-5° C. and then for 18 hours at room temperature. For working up, the reaction mixture is concentrated and the residue is taken up in ether. The ethereal solution is washed twice with water and three times with sodium chloride solution, dried over sodium sulfate, filtered and concentrated. The residue is recrystallised from isopropanol, affording 3,5-dinitro-4-[2-methoxyethyl-amino]-2-chlorobenzotrifluoride with a melting point of 104°-105° C.

The following compounds of the formula II are prepared in analogous manner:
3,5-dinitro-4-[3-ethoxypropylamino]-2-chlorobenzotrifluoride, m.p. 55°-56° C.;
3,5-dinitro-4-[3-isopropoxypropylamino]-2-chlorobenzotrifluoride, $n_D^{20} = 1.5426$;
3,5-dinitro-4-[3-methoxypropylamino]-2-chlorobenzotrifluoride, m.p. 77°-78° C.

The following compounds of the formula I are prepared in a manner analogous to that described above:

| R | X | n | melting point [°C.] |
|---|---|---|---|
| CH$_3$ | —O— | 3 | 73–74 |
| C$_2$H$_5$ | —O— | 3 | 90–91 |
| CH$_3$ | —S— | 2 | 70–71 |
| C$_2$H$_5$ | —S— | 2 | 55–56 |
| i-C$_3$H$_7$ | —O— | 3 | 92–94 |
| i-C$_3$H$_7$ | —S— | 2 | 63–65 |
| C$_2$H$_5$ | —O— | 2 | |
| sec.-C$_4$H$_9$ | —S— | 2 | 51–52 |
| i-C$_3$H$_7$ | —O— | 2 | |

EXAMPLE 2

Action against spider mites

*Phaseolus vulgaris* plants (dwarf beans) were infected 16 hours before the test with infested pieces of leaf from a mass culture of *Tetranychus urticae*. At the time of application, a large number of both eggs and all mobile stages are present on the plants. On a rotary table the plants infected with the mites were sprayed with about 100 ml of an aqueous emulsion preparation containing the active ingredient in a concentration of 800 ppm, such that the spray did not run off. The treated plants were then kept in a greenhouse compartment at about 25° C. Evaluation was made 7 days after the treatment in order to determine the percentage kill of eggs, larvae and adults. Compounds of the formula I according to Example 1 were very effective in this test.

EXAMPLE 3

Action against parasitic mites

Batches of about 50 mites in different stages (larvae, nymphs and imagines) were taken from hens infected with *Dermanyssus gallinae*. Each batch of mites was wetted in a dilution series with an aqueous emulsion, solution or suspension of the respective active ingredient to be tested. This was accomplished by pouring the liquid preparation containing the active ingredient over the batch in a test tube. The fluid was then absorbed by a cottonwool plug. The treated mites remained for 72 hours in the test tube. The minimum active ingredient concentration necessary for 100% kill of the treated mites was determined in comparison with untreated controls. Compounds of the formula I according to Example 1 were very effective in this test.

EXAMPLE 4

Action against ticks (A) *Rhipicephalus bursa*

Five adult ticks or 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton wool plug and placed on its head to enable the cotton wool to absorb the active ingredient emulsion. Evaluation of the action against adults was made after 2 weeks and of that against larvae after 2 days. Each test was repeated twice.

(B) *Boophilus microplus* (larvae)

Tests were carried out with 20 OP-sensitive and 20 OP-resistant larvae using a dilution series similar to that used in Test A. (The resistance refers to the tolerance towards diazinone). The compounds of the formula I according to Example 1 were effective in these tests against adults and larvae of *Rhipicephalus bursa* and OP-sensitive and OP-resistant larvae of *Boophilus microplus*.

EXAMPLE 5

Action against *Musca domestica*

50 g of freshly prepared CSMA nutrient substrate for maggots were charged into beakers. A specific amount of a 1% acetonic solution of the respective active ingredient was pipetted onto the nutrient substrate present in the beakers. The substrate was then thoroughly mixed and the acetone subsequently allowed to evaporate over a period of at least 20 hours.

Then 25 one-day-old maggots of *Musca domestica* were put into each of the beakers containing the treated nutrient substrate for testing with each active ingredient at one of its given concentrations. After the maggots had pupated, the pupae were separated from the substrate by flushing them out with water and then deposited in containers closed with a perforated top.

Each batch of flushed out pupae was counted to determine the toxic effect of the active ingredient on the maggot development. A count was then made after 10 days of the number of flies which had hatched out of the pupae. Evaluation was made on the basis of the minimum concentration of the tested compound that is still effective.

The compounds of the formula I according to Example 1 were very effective in this test.

EXAMPLE 6

Action against *Lucilia sericata*

1 ml of an aqueous formulation containing 0.5% of test substance was added at 50° C. to 9 ml of a culture medium. Then about 30 freshly hatched *Lucilia sericata* larvae were added to the culture medium, and the insecticidal action was determined after 48 and 96 hours by evaluating the mortality rate. In this test, compounds of the formula I according to Example 1 were very effective against *Lucilia sericata*.

EXAMPLE 7

Action against *Aedes aegypti*

Active ingredient concentrations of 10, 5 and 1 ppm respectively were obtained by pipetting a specific amount of a 0.1% solution of the active ingredient in acetone onto the surface of 150 ml of water in each of a number of beakers. After the acetone had evaporated, 30 to 40 three-day-old larvae of *Aedes aegypti* were put into each of the beakers containing the active ingredient solution. Mortality counts were made after 1, 2 and 5 days respectively.

In this test, compounds of the formula I according to Example 1 were very effective against *Aedes aegypti*.

What is claimed is:

1. A compound of the formula I

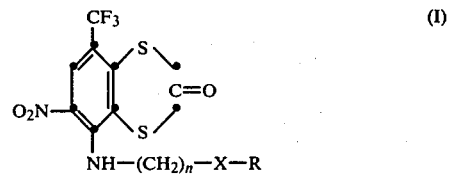

(I)

wherein X is —O— or —S—, R is $C_1$-$C_4$alkyl, and n is 2 or 3.

2. A compound according to claim 1 wherein X is —O— and R is methyl or ethyl.

3. The compound according to claim 2 of the formula

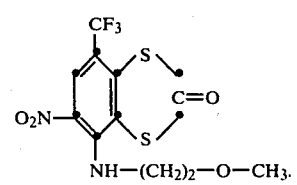

4. The compound according to claim 2 of the formula

5. The compound according to claim 2 of the formula

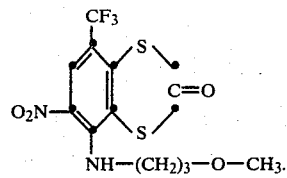

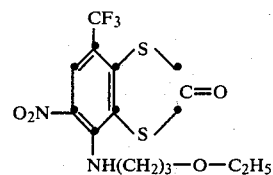

6. An insecticidal or acaricidal composition comprising (1) as active ingredient, an insecticidally or acaricidally effective amount of a compound according to claim 1, and (2) a carrier.

7. A method for controlling insects and acarids which are parasites of plants or animals, which comprises applying to said plants or animals an insecticidally or acaricidally effective amount of a compound according to claim 1.

8. A method according to claim 7 in which mites are controlled.

* * * * *